United States Patent
Elliott et al.

(10) Patent No.: US 8,192,730 B2
(45) Date of Patent: Jun. 5, 2012

(54) HAIR TREATMENT COMPOSITION COMPRISING SUGAR LACTONE

(75) Inventors: Rebecca Justine Elliott, Bebington (GB); Anand Ramchandra Mahadeshwar, Wirral (GB); Brodyck James Lachlan Royles, Wirral (GB); Laxmikant Tiwari, Southampton (GB)

(73) Assignee: Conopco, Inc., Englewood Cliffs, NJ (US)

( * ) Notice: Subject to any disclaimer, the term of this patent is extended or adjusted under 35 U.S.C. 154(b) by 1442 days.

(21) Appl. No.: 10/592,221

(22) PCT Filed: Feb. 18, 2005

(86) PCT No.: PCT/EP2005/001822
§ 371 (c)(1),
(2), (4) Date: Jun. 18, 2007

(87) PCT Pub. No.: WO2005/084623
PCT Pub. Date: Sep. 15, 2005

(65) Prior Publication Data
US 2008/0019938 A1    Jan. 24, 2008

(30) Foreign Application Priority Data
Mar. 8, 2004  (EP) ..................... 04251324

(51) Int. Cl.
*A61K 8/60*  (2006.01)
*A61Q 5/06*  (2006.01)
*A61Q 5/12*  (2006.01)

(52) U.S. Cl. .................. 424/70.27; 424/70.1

(58) Field of Classification Search ........... None
See application file for complete search history.

(56) References Cited

U.S. PATENT DOCUMENTS

| | | | |
|---|---|---|---|
| 3,470,887 A | 10/1969 | Kremer et al. | 132/7 |
| 3,822,238 A | 7/1974 | Blair | |
| 4,156,066 A | 5/1979 | Gould | |
| 4,156,067 A | 5/1979 | Gould | |
| 4,255,550 A | 3/1981 | Gould | |
| 4,460,571 A | 7/1984 | Gomez | |
| 4,743,673 A | 5/1988 | Johnston | |
| 4,786,493 A | 11/1988 | Smith | |
| 4,911,919 A * | 3/1990 | Patel et al. | 424/70.2 |
| 5,000,955 A | 3/1991 | Gould | |
| 5,507,970 A | 4/1996 | Ishikawa | |
| 5,547,988 A * | 8/1996 | Yu et al. | 514/557 |
| 5,641,477 A | 6/1997 | Syed et al. | 424/70.4 |
| 5,641,480 A * | 6/1997 | Vermeer | 424/70.24 |
| 5,747,016 A * | 5/1998 | Yui et al. | 424/401 |
| 5,833,968 A | 11/1998 | Keil | |
| 6,384,079 B1 | 5/2002 | Yu et al. | 514/577 |
| 7,988,954 B2 | 8/2011 | Chandra | |
| 2003/0105169 A1 | 6/2003 | Lennon | 516/53 |
| 2005/0255070 A1 | 11/2005 | Albano | |

FOREIGN PATENT DOCUMENTS

| | | |
|---|---|---|
| EP | 455 185 | 11/1991 |
| EP | 0619111 A1 | 10/1994 |
| EP | 530 974 | 7/1995 |
| FR | 2899464 | 10/2007 |
| GB | 915 816 | 1/1963 |
| GB | 1076420 | 9/1964 |
| JP | 2001055571 | 2/2001 |
| JP | 2001233746 | 8/2001 |
| JP | 2002356408 | 12/2002 |
| JP | 2006232820 | 9/2006 |
| JP | 2006282566 | 10/2006 |
| WO | WO9104007 | 4/1991 |
| WO | WO9500104 | 1/1995 |
| WO | 00/42978 | 7/2000 |
| WO | WO0042978 | 7/2000 |
| WO | 02/43675 | 6/2002 |
| WO | 2004/037305 | 5/2004 |
| WO | WO2004037217 A1 | 5/2004 |
| WO | WO2006061678 A1 | 6/2006 |
| WO | WO2006134409 A2 | 12/2006 |
| WO | WO2008012733 A2 | 1/2008 |

OTHER PUBLICATIONS

PCT International Search Report in a PCT application PCT/EP2005/001822.
PCT International Search Report in a PCT application PCT/EP2005/001408.
Derwent Abstract—JP 2002 356408 published Dec. 13, 2002.
Derwent Abstract—JP 2001 233746 published Aug. 28, 2001.
Co-pending application: Applicant: Chandra et al., U.S. Appl. No. 10/592,225.
Scherz, Food Composiition and Nutrition Tables, Food Composiition and Nutrition Tables, ., ., 1089, Nedogarn Scientific Publishers.
Cashman, Milk minerals (including trace elements) and bone health, Milk minerals (including trace elements) and bone health, May 31, 2006, vol. 16 No. 11, 1389-1398, Elsvier.
Co-pending Application: Applicant: Paul; U.S. Appl. No. 12/531,084, filed Jan. 14, 2010.
PCT International Search Report in PCT application PCT/EP2008/050822; dated Jun. 13, 2008.
European Search Report in EP application EP 07 10 4155; dated: Aug. 31, 2007.
Co-pending Application: Applicant: Pye et al.,; U.S. Appl. No. 12/682,060, filed Sep. 16, 2010.
PCT International Search Report in PCT application PCT/EP2008/063401; dated Jan. 29, 2009.
Co-pending Application: Applicant: Pye et al., U.S. Appl. No. 12/933,811, filed Oct. 28, 2010.
PCT International Search Report in PCT application PCT/EP2009/053015; dated Jun. 29, 2010.

* cited by examiner

*Primary Examiner* — Shanon A Foley
(74) *Attorney, Agent, or Firm* — Ronald A. Koatz

(57) ABSTRACT

A hair treatment composition for straightening hair. The composition comprises: i) 0.1 to 7.9 wt % of the total formulation of a sugar lactone; and ii) cationic surfactant of formula (1): $[N(R_1)(R_2)(R_3)(R_4)]+(X)^-$ in which $R_1$, $R_2$, $R_3$, and $R_4$ are independently selected from (a) an aliphatic group of from 1 to 22 carbon atoms, or (b) an aromatic, alkoxy, polyoxyalkylene, alkylamido, hydroxyalkyl, aryl or alkylaryl group having up to 22 carbon atoms; and X is a salt-forming anion selected from halogen, acetate, citrate, lactate, glycolate, phosphate nitrate, sulphate, and alkylsulphate.

8 Claims, No Drawings

HAIR TREATMENT COMPOSITION COMPRISING SUGAR LACTONE

FIELD OF THE INVENTION

The present invention relates to conditioner compositions. In particular it relates to a conditioner composition that straightens hair.

BACKGROUND AND PRIOR ART

Hair straightening compositions have been around for some time. Many of the compositions that are on the market are based on chemical treatment of the hair in a two-step process using thiol- or hydroxide-based reducing agents followed by a neutralisation or oxidation step. Such systems have various negatives associated with them; in that the process itself takes a relatively long time and is difficult to conduct, in many instances this straightening process is undertaken by a qualified hairdresser in a professional salon. Furthermore the straightening process damages the hair, has an unpleasant odor and can cause irritation to the scalp.

Sugars have been used in styling compositions as disclosed in DE 697 634 and U.S. Pat. No. 4,911,919

We have now found a way of straightening hair by using a conditioning formulation without the above mentioned negatives.

DESCRIPTION OF THE INVENTION

The present invention relates to a hair treatment composition comprising:
i) 0.1 to 7.9 wt % of the total formulation of a sugar lactone; and
ii) cationic surfactant of formula 1:

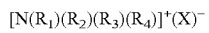  Formula 1 in which $R_1$, $R_2$, $R_3$, and $R_4$ are independently selected from (a) an aliphatic group of from 1 to 22 carbon atoms, or (b) an aromatic, alkoxy, polyoxyalkylene, alkylamido, hydroxyalkyl, aryl or alkylaryl group having up to 22 carbon atoms; and X is a salt-forming anion selected from halogen, acetate, citrate, lactate, glycolate, phosphate nitrate, sulphate, and alkylsulphate.

A further aspect of this invention is a method of straightening hair without mechanical intervention in which a composition comprising a sugar lactone is applied to the hair.

Also described is the use of a sugar lactone to straighten hair.

DETAILED DESCRIPTION

Unless otherwise specified, all percentages by weight are based upon the total weight of the composition.

Compositions according to the invention are preferably aqueous compositions intended to be applied to the hair after shampooing and rinsing. They are massaged into wet hair and scalp, preferably followed by further rinsing with water prior to drying the hair. By aqueous composition, it is meant that the compositions of the invention comprise 60% by weight or more of water, preferably 70% or more, more preferably 80% or more.

Cationic Surfactants

Compositions according to the invention comprise one or more cationic conditioning surfactants, which are cosmetically acceptable and suitable for topical application to the hair.

Cationic conditioning surfactants useful in compositions of the invention contain amino or quaternary ammonium hydrophilic moieties, which are positively charged when dissolved in the aqueous composition of the present invention.

The cationic surfactants for use with the invention are those corresponding to formula 1:

  Formula 1 in which $R_1$, $R_2$, $R_3$, and $R_4$ are independently selected from (a) an aliphatic group of from 1 to 22 carbon atoms, or (b) an aromatic, alkoxy, polyoxyalkylene, alkylamido, hydroxyalkyl, aryl or alkylaryl group having up to 22 carbon atoms; and X is a salt-forming anion such as those selected from halogen (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g. those of about 12 carbons, or higher, can be saturated or unsaturated.

Preferred cationic surfactants for conditioner compositions of the present invention are those according to formula 1 in which $R_1$ is a $C_{16}$ to $C_{22}$ alkyl chain and $R_2$, $R_3$ and $R_4$ are independently selected from the group consisting of $CH_3$ and $CH_2CH_2OH$.

Another preferred class of cationic conditioning surfactants has $R_1$ and $R_2$ independently selected from $C_{16}$ to $C_{22}$ saturated or unsaturated, preferably saturated, chains and with $R_3$ and $R_4$ independently selected from the group consisting of $CH_3$ and $CH_2CH_2OH$, preferably $CH_3$.

Particularly preferred cationic systems are those comprising both dimethyl and trimethyl quaternary ammonium groups described above.

Another suitable class of cationic conditioning surfactants has $R_1$ and $R_2$ independently selected from $C_{16}$ to $C_{22}$ hydrocarbyl chains comprising at least one ester linkage in both $R_1$ and $R_2$, and with $R_3$ and $R_4$ independently selected from the group consisting of $CH_3$ and $CH_2CH_2OH$. Wherein $R_1$ and $R_2$ are independently selected from $C_{15}$ to $C_{21}$ saturated or unsaturated alkyl chains. X is preferably a halide, a methosulphate anion or mixtures thereof. Chloride is particularly preferred.

Examples of preferred cationic surfactants used alone or in a mixture include:
cetyltrimethylammonium chloride and bi-phenyltrimethylammonium chloride and di-hydrogenated tallow dimethylammonium chloride.

Particularly preferred systems are those comprising cetyltrimethylammonium chloride and dioctadecyldimethyl ammonium chloride in a ratio (by weight) from 1:3 to 3:1 or cetyltrimethylammonium chloride and di-hardenedtallowdimethyl ammonium chloride in a ratio (by weight) from 1:3 to 3:1, more preferably from 3:1 to 1:1, most preferably from 3:1 to 2:1.

The level of cationic surfactant in the formulation is preferably from 0.1 to 15 wt % of the total composition, more preferably from 0.5 to 10 wt %, most preferably from 2 to 6 wt %.

Monosaccharide

The composition of the invention comprise a sugar lactone, preferably gluconolactone, especially glucono-delta-lactone.

The level of gluconolactone is from 0.1 to 7.9 wt % preferably greater than 0.5 wt % of the total composition, more preferably the level of gluconolactone is from 1 wt % to 7 wt % of the total composition, most preferably from 2 to 6 wt %.

The weight ratio of gluconolactone to total cationic surfactant is preferably in the range 1:3 to 10:1 (based on active wt %), more preferably 1:1 to 8:1, most preferably 2:1 to 5:1.

Wax

Compositions of the invention preferably comprise a wax. Beeswax is a preferred wax in the composition as it further straightens the hair without any sensory negatives.

The beeswax is preferably in a particulate form as particles with a median ($D_{50}$) diameter of 50 micrometres or less, preferably 20 micrometres or less, more preferably 10 micrometres or less and even more preferably 1 micrometre or less.

The beeswax is suitably present at from 0.2% to 4% by weight of the composition, preferably from 0.4% to 3%, more preferably from 0.6% to 2%. The beeswax may be pre-formed into an emulsion or dispersion before addition to the rest of the composition.

Fatty Material

Conditioner compositions of the invention preferably comprise at least one fatty material. The combined use of fatty materials and cationic surfactants in the conditioning compositions is believed to lead to the formation of a structured lamellar or liquid crystal phase, in which the cationic surfactant is dispersed.

By "fatty material" is meant a fatty alcohol, an alkoxylated fatty alcohol, a fatty acid or a mixture thereof.

Preferably, the alkyl chain of the fatty material is fully saturated.

Suitable fatty materials comprise from 12 to 22 carbon atoms, preferably from 16 to 18 carbon atoms. Examples of suitable fatty alcohols include cetyl alcohol, stearyl alcohol and mixtures thereof. The use of these materials is also advantageous in that they contribute to the overall conditioning properties of compositions of the invention.

Alkoxylated (e.g. ethoxylated or propoxylated) fatty alcohols having from about 12 to about 22 carbon atoms in the alkyl chain can be used in place of, or in addition to, the fatty alcohols themselves. Suitable examples include ethylene glycol cetyl ether, polyoxyethylene (2) stearyl ether, polyoxyethylene (4) cetyl ether, and mixtures thereof. Particularly preferred is cetearyl alcohol (a 1:2 mixture of cetyl alcohol: stearyl alcohol).

The level of fatty material in conditioners of the invention is suitably from 0.5 to 10, preferably from 1 to 6 percent by weight of the total composition. The weight ratio of cationic surfactant to fatty alcohol is suitably from 10:1 to 1:10, preferably from 4:1 to 1:8, optimally from 1:1 to 1:7.

Alkali Metal Salt

The compositions may contain an alkali metal halide or mixtures thereof.

Preferred alkali metals are sodium or potassium and preferred halides are chlorides and bromides. Particularly preferred is potassium chloride.

Conditioning Oil

A preferred component of compositions according to the invention is a hydrophobic conditioning oil. In order for such an oil to exist in the preferred form as discrete droplets in the compositions according to the invention, it must be water-insoluble. By water-insoluble it is meant that the solubility in water at 25° C. is 0.01% by weight or less.

It is preferred if the conditioning oil is non-volatile, by which it is meant that the vapour pressure of the oil at 25° C. is less than 10 Pa.

As used herein, the term "conditioning oil" includes any material, which is used to give a particular conditioning benefit to hair. For example, suitable materials are those which deliver one or more benefits relating to shine, softness, combability, wet-handling, anti-static properties, protection against damage, body, volume, styleability and manageability.

Suitable hydrophobic conditioning oils are selected from hydrocarbon oils, fatty esters, silicone oils and mixtures thereof.

Hydrocarbon oils include cyclic hydrocarbons, straight chain aliphatic hydrocarbons (saturated or unsaturated), and branched chain aliphatic hydrocarbons (saturated or unsaturated). Straight chain hydrocarbon oils will preferably contain from about 12 to about 30 carbon atoms. Branched chain hydrocarbon oils can and typically may contain higher numbers of carbon atoms. Also suitable are polymeric hydrocarbons of alkenyl monomers, such as $C_2$-$C_6$ alkenyl monomers. These polymers can be straight or branched chain polymers. The straight chain polymers will typically be relatively short in length, having a total number of carbon atoms as described above for straight chain hydrocarbons in general. The branched chain polymers can have substantially higher chain length. The number average molecular weight of such materials can vary widely, but will typically be up to about 2000, preferably from about 200 to about 1000, more preferably from about 300 to about 600.

Specific examples of suitable hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used. Exemplary branched-chain isomers are highly branched saturated or unsaturated alkanes, such as the permethyl-substituted isomers, e.g. the permethyl-substituted isomers of hexadecane and eicosane, such as 2,2-, 4,4-, 6,6-, 8,8-dimethyl-10-methylundecane and 2,2-, 4,4-, 6,6-dimethyl-8-methylnonane, sold by Permethyl Corporation. A further example of a hydrocarbon polymer is polybutene, such as the copolymer of isobutylene and butene. A commercially available material of this type is L-14 polybutene from Amoco Chemical Co. (Chicago, Ill., U.S.A.).

Particularly preferred hydrocarbon oils are the various grades of mineral oils. Mineral oils are clear oily liquids obtained from petroleum oil, from which waxes have been removed, and the more volatile fractions removed by distillation. The fraction distilling between 250° C. to 300° C. is termed mineral oil, and it consists of a mixture of hydrocarbons ranging from $C_{16}H_{34}$ to $C_{21}H_{44}$. Suitable commercially available materials of this type include Sirius M85 and Sirius M125, all available from Silkolene.

Suitable fatty esters are characterised by having at least 10 carbon atoms, and include esters with hydrocarbyl chains derived from fatty acids or alcohols, e.g. monocarboxylic acid esters, polyhydric alcohol esters, and di- and tricarboxylic acid esters. The hydrocarbyl radicals of the fatty esters hereof can also include or have covalently bonded thereto other compatible functionalities, such as amides and alkoxy moieties, such as ethoxy or ether linkages.

Monocarboxylic acid esters include esters of alcohols and/or acids of the formula R'COOR in which R' and R independently denote alkyl or alkenyl radicals and the sum of carbon atoms in R' and R is at least 10, preferably at least 20.

Specific examples include, for example, alkyl and alkenyl esters of fatty acids having aliphatic chains with from about 10 to about 22 carbon atoms, and alkyl and/or alkenyl fatty alcohol carboxylic acid esters having an alkyl and/or alkenyl alcohol-derived aliphatic chain with about 10 to about 22 carbon atoms, benzoate esters of fatty alcohols having from about 12 to 20 carbon atoms.

The monocarboxylic acid ester need not necessarily contain at least one chain with at least 10 carbon atoms, so long as the total number of aliphatic chain carbon atoms is at least 10. Examples include isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate.

Di- and trialkyl and alkenyl esters of carboxylic acids can also be used. These include, for example, esters of $C_4$-$C_8$ dicarboxylic acids such as $C_1$-$C_{22}$ esters (preferably $C_1$-$C_6$) of succinic acid, glutaric acid, adipic acid, hexanoic acid, heptanoic acid, and octanoic acid. Examples include diisopropyl adipate, diisohexyl adipate, and diisopropyl sebacate. Other specific examples include isocetyl stearoyl stearate, and tristearyl citrate.

Polyhydric alcohol esters include alkylene glycol esters, for example ethylene glycol mono- and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol monostearate, ethoxylated propylene glycol monostearate, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, polyoxyethylene sorbitan fatty acid esters and mono-, di-and triglycerides.

Particularly preferred fatty esters are mono-, di- and triglycerides, more specifically the mono-, di-, and tri-esters of glycerol and long chain carboxylic acids such as $C_1$-$C_{22}$ carboxylic acids. A variety of these types of materials can be obtained from vegetable and animal fats and oils, such as coconut oil, castor oil, safflower oil, sunflower oil, cottonseed oil, corn oil, olive oil, cod liver oil, almond oil, avocado oil, palm oil, sesame oil, peanut oil, lanolin and soybean oil. Synthetic oils include triolein and tristearin glyceryl dilaurate.

Specific examples of preferred materials include cocoa butter, palm stearin, sunflower oil, soybean oil and coconut oil.

The oil may be blended with other materials in the discrete droplets present in compositions according to the invention.

The total amount of hydrophobic conditioning oil present in the composition is preferably from 0.1% to 10% by weight of the total composition more preferably from 0.2% to 6%, most preferably 0.5% to 4%.

Silicone Conditioning Oils

Preferred hydrophobic conditioning oils for use in compositions according to the invention are silicones.

Suitable silicones for use as conditioning oils include polydiorganosiloxanes, in particular polydimethylsiloxanes which have the CTFA designation dimethicone. Also suitable for use in compositions of the invention are polydimethyl siloxanes having hydroxyl end groups, which have the CTFA designation dimethiconol.

It is preferred if the silicone oil also comprises a functionalised silicone. Suitable functionalised silicones include, for example, amino-, carboxy-, betaine-, quaternary ammonium-, carbohydrate-, hydroxy- and alkoxy-substituted silicones. Preferably, the functionalised silicone contains multiple substitutions.

For the avoidance of doubt, as regards hydroxyl-substituted silicones, a polydimethylsiloxane merely having hydroxyl end groups (which have the CTFA designation dimethiconol) is not considered a functionalised silicone within the present invention. However, a polydimethylsiloxane having hydroxyl substitutions along the polymer chain is considered a functionalised silicone.

Preferred functionalised silicones are amino-functionalised silicones. Suitable amino functionalised silicones are described in EP 455,185 (Helene Curtis) and include trimethylsilylamodimethicone.

An example of a commercially available amino-functionalised silicone useful in the silicone component of the composition of the invention is DC-8566 available from Dow Corning (INCI name: dimethyl, methyl(aminoethylaminoisobutyl)siloxane). This has a weight percent amine functionality of about 1.4%.

By "amino functional silicone" is meant a silicone containing at least one primary, secondary or tertiary amine group, or a quaternary ammonium group. Examples of suitable amino functional silicones include: polysiloxanes having the CTFA designation "amodimethicone". Specific examples of amino functional silicones suitable for use in the invention are the aminosilicone oils DC-8220, DC-8166, DC-8466, and DC-8950-114 (all ex Dow Corning), and GE 1149-75 (ex General Electric Silicones). Suitable quaternary silicone polymers are described in EP-A-0 530 974. A preferred quaternary silicone polymer is K3474, ex Goldschmidt.

Another preferred functional silicone for use as a component in the hydrophobic conditioning oil is an alkoxy-substituted silicone. Such molecules are known as silicone copolyols and have one or more polyethyleneoxide or polypropyleneoxide groups bonded to the silicone polymer backbone, optionally through an alkyl linking group.

Suitable silicone copolyols have an HLB of 10 or less, preferably 7 or less, more preferably 4 or less. A suitable silicone copolyol material is DC5200, known as Lauryl PEG/PPG-18/18 methicone (INCI name), available from Dow Corning.

Also suitable for use with the present invention is a copolymer of divinyldimethicone and dimethicone. A suitable commercial material supplied as an aqueous emulsion is Dow Corning HMW 2220.

It is preferred to use a combination of functional and non-functional silicones as the hydrophobic silicone conditioning oil. Preferably the silicones are blended into common droplets prior to incorporation into compositions according to the invention.

It is preferred if silicones are added to the compositions of the invention as pre-formed emulsions, more preferably as microemulsions.

Further Ingredients

Compositions according to the invention may also incorporate other cosmetically suitable ingredients, preferably at a level of 2% by weight or less. Suitable ingredients include: viscosity modifiers, preservatives, colouring agents, polyols such as glycerine and polypropylene glycol, chelating agents such as EDTA, antioxidants, fragrances, antimicrobials, anti-dandruff agents, cationic conditioning polymers, styling ingredients, sunscreens, proteins and hydrolysed proteins.

Although the product may be in any form suitable for application to the hair it is preferable if it is a rinse off product. Products used to condition the hair are especially preferred.

In use the composition of the invention is applied to the hair and then preferably rinsed off up to 30 minutes after application, more preferably this product is rinsed off 10 minutes after application.

The invention will now be illustrated with aid of the following Examples. Examples of the invention are illustrated by a number, comparative Examples are illustrated by a letter.

The following examples, which were made, are shown as illustrations only and are not intended to limit the scope of the invention.

In Vitro Tests

Hair switches were washed twice with shampoo base and left to dry at 50% RH and 23° C. overnight. A photograph was taken. The switches were washed twice with 1.0 g shampoo base and combed with a wide-tooth comb. The switches were then treated with 2.0 g conditioner formulation, as detailed in the table of examples, for 2 minutes. The conditioner was rinsed off and the switches combed with a wide-tooth comb and allowed to dry at 50% RH and 23° C. overnight. The switches were photographed. Panellists assessed photographs of the switches taken before and after treatment, and observed a straightening benefit compared with switches treated with a standard conditioner composition.

significance compared with formulation A. Formulation 4 gave a greater fluff benefit than formulation 5, which gave a greater fluff benefit than formulation 2, which gave a greater fluff benefit than formulation 3, which gave a greater fluff benefit than formulation 1.

Furthermore, formulations 1 to 5 delivered a decrease in waviness. Formulations 2, 3, 4 and 5 gave a decrease in waviness at 99% significance. Formulation 5 gave a greater waviness benefit than formulation 3, which gave a greater waviness benefit than formulation 2, which gave a greater waviness benefit than formulation 4, which gave a greater waviness benefit than formulation 1.

| CTFA/Chemical Name | Trade name | Manufacturer | Base formulation Formulation A (control) % (w/w) | Prototype formulation # 1% (w/w) |
|---|---|---|---|---|
| Cetyl Trimethyl Ammonium Chloride (50% AI) | Arquad 16-50 | Akzo | 3.24 (1.62 wt % active) | 3.24 (1.62 wt % active) |
| Dioctadecyl Dimethyl Ammonium Chloride (75% AI) | Arquad 2HT-75PG | Akzo | 1.08 (0.81 wt % active) | 1.08 (0.81 wt % active) |
| Cetearyl Alcohol | Laurex CS or | Albright and Wilson Ltd. | 5.00 | 5.00 |
| Dimethiconol (and) TEA Dodecyl Benzene Sulphonate (60% AI) | DC-1785 | Dow Corning | 3.33 (2.00 wt % active) | 3.33 (2.00 wt % active) |
| Cyclomethicone DC 245 | DC 245 | Dow Corning | 2.00 | 2.00 |
| Hydroxyethyl Cellulose | Natrosol 250HHBR | Hercules | 0.20 | 0.20 |
| Methyl-p-hydroxy benzoate | Nipagin M or | Nipa Lab | 0.20 | 0.20 |
| Formaldehyde | Formalin | Klang-Wanit | 0.10 | 0.10 |
| Gluconolactone | | | — | 1.00 |
| Divinyldimethicone | HMW2220 | Dow Corning | — | — |
| Beeswax | | | — | — |

| | Prototype formulation # | | | |
|---|---|---|---|---|
| CTFA/Chemical Name | 2% (w/w) | 3% (w/w) | 4% (w/w) | 5% (w/w) |
| Cetyl Trimethyl Ammonium Chloride (50% AI) | 3.24 (1.62 wt % active) | 3.24 (1.62 wt % active) | 3.24 (1.62 wt % active) | 3.24 (1.62 wt % active) |
| Dioctadecyl Dimethyl Ammonium Chloride (75% AI) | 1.08 (0.81 wt % active) | 1.08 (0.81 wt % active) | 1.08 (0.81 wt % active) | 1.08 (0.81 wt % active) |
| Cetearyl Alcohol | 5.00 | 5.00 | 5.00 | 5.00 |
| Dimethiconol (and) TEA Dodecyl Benzene Sulphonate (60% AI) | 3.33 (2.00 wt % active) | 3.33 (2.00 wt % active) | 3.33 (2.00 wt % active) | 3.33 (2.00 wt % active) |
| Cyclomethicone DC 245 | 2.00 | 2.00 | — | — |
| Hydroxyethyl Cellulose | 0.20 | 0.20 | 0.20 | 0.20 |
| Methyl-p-hydroxy benzoate | 0.20 | 0.20 | 0.20 | 0.20 |
| Formaldehyde | 0.10 | 0.10 | 0.10 | 0.10 |
| Gluconolactone | 4.00 | 6.00 | 4.00 | 4.00 |
| Divinyldimethicone | — | — | 2.00 | 2.00 |
| Beeswax | — | — | — | 1.50 |

Formulations 1 to 5 delivered an increase in straightening compared with formulation A (control). Formulations 2, 3 and 5 gave straightening benefit at 99% significance. Formulation 4 gave straightening benefit at 95% significance. Formulation 5 gave a greater straightening benefit than formulation 3, which gave a greater straightening benefit than formulation 2, which gave a greater straightening benefit than formulation 4, which gave a greater straightening benefit than formulation 1.

Furthermore, formulations 1 to 5 delivered a decrease in fluff. Formulations 2, 4 and 5 gave a decrease in fluff at 99%

In Vivo Tests

Formulations 5, 6 and 7 were evaluated by panellists in a monadic home-use test. The number of panellists evaluating each conditioner formulation was 50. Five prototype formulations and a control formulation were tested. Total number of consumers=300. The test duration was 2 weeks, with consumers using the prototype formulation in a minimum of 6 washes. A standard shampoo formulation was supplied for use immediately prior to application of the conditioner formulation.

| CTFA/Chemical Name | Trade name | Manufacturer | Base formulation Formulation B (control) % (w/w) | Prototype formulation # 5 (cell 3) % (w/w) | 6 (cell 2) % (w/w) | 7 (cell 4-DMQ) % (w/w) |
|---|---|---|---|---|---|---|
| Cetyl Trimethyl Ammonium Chloride (50% AI) | Arquad 16-50 | Akzo | 1.75 (0.875 wt % active) | 1.75 (0.875 wt % active) | 1.75 (0.875 wt % active) | 3.24 (1.62 wt % active) |
| Dioctadecyl Dimethyl Ammonium Chlori (75% AI) | Arquad 268-75PG | Akzo | 0.50 (0.375 wt % active) | 0.50 (0.375 wt % active) | 0.50 (0.375 wt % active) | 1.08 (0.810 wt % active) |
| Cetearyl Alcohol | Hydrenol MY | Cognis Thai | 4.00 | 4.00 | 4.00 | 5.00 |
| Dimethiconol (and) TEA Dodecyl Benzene Sulphonate (60% AI) | DC-1785 | Dow Corning | 3.33 (2.00 wt % active) | — | — | — |
| Cyclomethicone DC 245 | DC 245 | Dow Corning | — | — | — | 2.00 |
| Hydroxyethyl Cellulose | Natrosol 250HHBR | Hercules | 0.20 | 0.20 | 0.20 | 0.20 |
| Methyl-p-hydroxy benzoate | Nipagin M | Nipa Lab | 0.20 | 0.20 | 0.20 | 0.20 |
| Formaldehyde | Formalin | Klang-Wanit | 0.10 | 0.10 | 0.10 | 0.10 |
| Gluconolactone | | | — | 4.00 | 4.00 | 4.00 |
| Divinyldimethicone | HMW2220 | Dow Corning | — | 2.00 | 2.00 | 2.00 |
| Beeswax | | | — | 1.50 | — | 1.50 |

Formulations 5, 6 and 7 gave significant benefit on a number of visual attributes when compared with formulation B (control). In particular, formulation 5 gave straighter hair at 90% significance and a reduced number of curls at 90% significance. Formulation 6 gave a reduced depth of curl at 95% significance.

The invention claimed is:

1. A method of straightening hair comprising the steps of
   (a) applying to the hair an aqueous composition comprising:
      (i) 0.1 to 7.9 wt % of the total formulation of a sugar lactone;
      ii) cationic surfactant of formula 1:

[N(R$_1$)(R$_2$)(R$_3$)(R$_4$)]$^+$(X)$^-$     Formula I in which R$_1$, R$_2$, R$_3$, and R$_4$ are independently selected from (a) an aliphatic group of from 1 to 22 carbon atoms, or (b) an aromatic, alkoxy, polyoxyalkylene, alkylamido, hydroxyalkyl, aryl or alkylaryl group having up to 22 carbon atoms; and X is a salt-forming anion selected from halogen, acetate, citrate, lactate, glycolate, phosphate nitrate, sulphate, and alkylsulphate; and
      (iii) water;
   wherein the composition is rinsed from the hair up to 30 minutes after application; and wherein the sugar lactone within the composition is gluconolactone and wherein the weight ratio of glucanolactone to total cationic surfactant is in the range of 1:3 to 10:1.

2. A method according to claim 1 in which the level of sugar lactone is greater than 0.5 wt % of the total composition, and wherein water is present in the composition in an amount of at least 70% by weight of the total composition.

3. A method according to claim 2 in which the level of sugar lactone is from 2 wt % to 6 wt % of the total composition.

4. A method according to claim 1 wherein the level of cationic surfactant is from 0.1 wt % to 15 wt % of the total composition.

5. A method according to claim 1 in which the composition further comprises a wax.

6. A method according to claim 5 in which the wax is beeswax, present in an amount of 0.2 to 4% by weight of the composition.

7. A method according to claim 1 in which the composition is rinsed off.

8. A method of straightening hair according to claim 1 in which hair is straightened without mechanical intervention.

* * * * *